US010525081B2

(12) United States Patent
Ray et al.

(10) Patent No.: US 10,525,081 B2
(45) Date of Patent: Jan. 7, 2020

(54) PROGRESSIVELY TUMORIGENIC CELL LINES

(71) Applicant: Grove City College, Grove City, PA (US)

(72) Inventors: Durwood B. Ray, Grove City, PA (US); David Jones, Grove City, PA (US)

(73) Assignee: Grove City College, Grove City, PA (US)

( * ) Notice: Subject to any disclaimer, the term of this patent is extended or adjusted under 35 U.S.C. 154(b) by 18 days.

(21) Appl. No.: 15/664,305

(22) Filed: Jul. 31, 2017

(65) Prior Publication Data

US 2018/0071338 A1    Mar. 15, 2018

Related U.S. Application Data

(60) Provisional application No. 62/369,638, filed on Aug. 1, 2016.

(51) Int. Cl.
*A61K 35/13*   (2015.01)
*A01K 67/027*  (2006.01)
*C12N 5/09*    (2010.01)
*G01N 33/50*   (2006.01)

(52) U.S. Cl.
CPC .......... *A61K 35/13* (2013.01); *A01K 67/0271* (2013.01); *C12N 5/0693* (2013.01); *G01N 33/5044* (2013.01); *A01K 2227/105* (2013.01); *A01K 2267/0331* (2013.01)

(58) Field of Classification Search
None
See application file for complete search history.

(56) References Cited

PUBLICATIONS

Navale (2013) "Animal Models of Cancer: A Review", International Journal of Pharmaceutical Sciences and Research, 4(1): 19-28. (Year: 2013).*

* cited by examiner

*Primary Examiner* — Robert M Kelly
(74) *Attorney, Agent, or Firm* — Mintz, Levin, Cohn, Ferris, Glovsky and Popeo P.C.

(57) ABSTRACT

Provided herein, inter alia, are tumorigenic cell lines and methods for using the same for deriving a series of cell culture and non-human animal-based models which exhibit increasingly aggressive tumorigenic potential as well as use of the same for evaluating the anti-neoplastic properties of candidate therapeutic agents.

13 Claims, 4 Drawing Sheets
(2 of 4 Drawing Sheet(s) Filed in Color)
Specification includes a Sequence Listing.

FIG. 2A 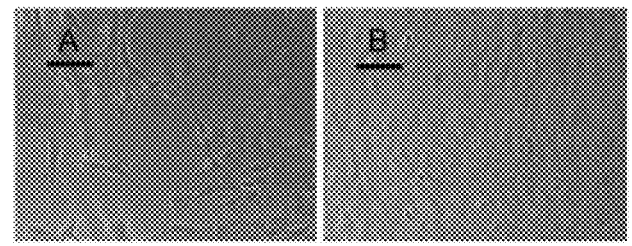 FIG. 2B
FIG. 2C 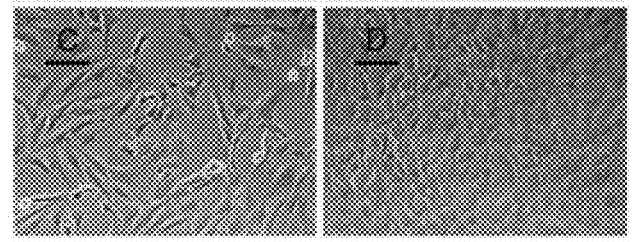 FIG. 2D
FIG. 2E 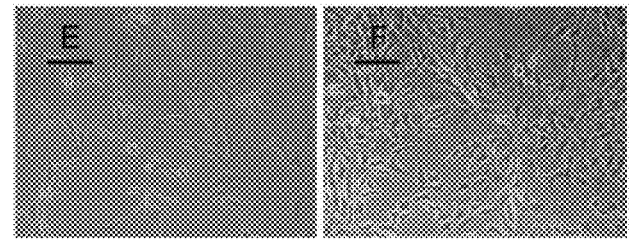 FIG. 2F
FIG. 2G 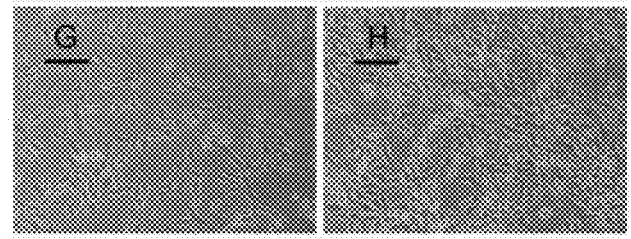 FIG. 2H
FIG. 2I 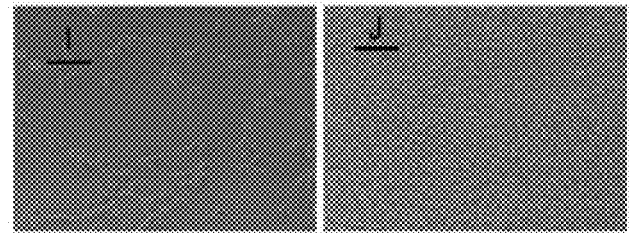 FIG. 2J
FIG. 2K 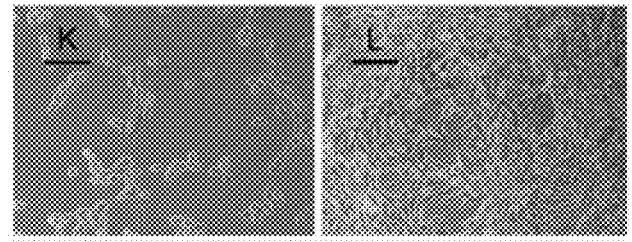 FIG. 2L
FIG. 2M 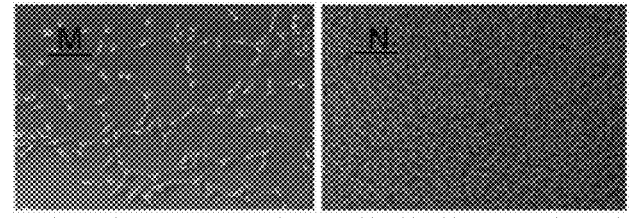 FIG. 2N

FIG. 3

| DNA added | NIH/3T3 | | | | T2-A | | | | T4-PA | | | | Mouse Liver | | Human Placenta | |
|---|---|---|---|---|---|---|---|---|---|---|---|---|---|---|---|---|
| | | | | | M | | H | | M | | H | | M | H | M | H |
| HRAS Primer Set | 1 | 2 | 3 | 4 | 5 | 6 | 7 | 8 | 9 | 10 | 11 | 12 | 13 | 14 | | |
| Human 1150bp | | | | | | | | | | | | | | | | |
| Mouse 216bp | | | | | | | | | | | | | | | | |

PROGRESSIVELY TUMORIGENIC CELL LINES

CROSS-REFERENCE TO RELATED APPLICATIONS

This application claims priority to U.S. provisional patent application Ser. No. 62/369,638, filed on Aug. 1, 2016, the content of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under Grant #8602787 awarded by the National Science Foundation. The government has certain rights in the present invention.

SUBMISSION OF SEQUENCE LISTING ON ASCII TEXT FILE

The Sequence Listing submitted in an ASCII text file, in accordance with 37 C.F.R. § 1.821(c) and (e), is incorporated herein by reference. The text file name is 051004_501001US_Sequence_Lisiting_11062017.TXT, the date of creation of the text file is Nov. 13, 2017, and the size of the ASCII text file is 904 bytes.

FIELD OF THE INVENTION

Provided herein, inter alia, are tumorigenic cell lines and methods for using the same for deriving a series of cell culture and non-human animal-based models which exhibit increasingly aggressive tumorigenic potential as well as use of the same for evaluating the anti-neoplastic properties of candidate therapeutic agents.

BACKGROUND OF THE INVENTION

Cancer remains a pressing medical and public health problem, in spite of decades of research into the molecular and genetic mechanisms underlying the development of this disease. It is well established that human cancers develop in a multistep sequence with environmental influences including chemical, physical, and viral agents being major etiological contributors. Numerous transitions occur in a "tumorigenic progression" as cells change from "normal" to "immortalized" to "transformed" and finally to the "metastatic state." These changes that produce tumors all occur in a variety of in vivo microenvironments. Recent studies indicate that cancer cells release exosomes that migrate ahead and attach at distant locations and somehow prepare these microenvironments for the progressing tumorigenic cells to settle into as they arrive to establish a metastatic tumor. The classical textbook view of a gradual accumulation of genomic alterations in this progression has been enlightened using next generation whole genome sequencing (WGS) and spectral karyotyping (SKY) with the recent description of stochastic cancer genome fragment rearrangements.

Current studies of transformation and tumor progression often rely on the use of primary embryonic cells or cell lines as a model to evaluate the myriad effects of various treatments on cells progressing from normal to pre-malignant to malignant and even metastatic potential. However, model systems that provide for the ability to evaluate the anti-neoplastic potential of candidate therapeutic agents against a series of increasingly aggressive tumors which are derived sequentially from a single progenitor cell type are needed. As the progressively aggressive tumors produced by this model would be derived from the same progenitor cell type in vivo in a variety of actual non-human animal microenvironments, such a model would more closely recapitulate the normal transitions observed in human cancers as they progress in vivo from localized tumors into a more virulent metastatic state. The ability to preserve and use these cells from these tumors for further characterization and studies of anti-neoplastic agents illustrates the uniqueness of this series of cells that have been generated by this novel serially extended in vivo/in vitro approach.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF SUMMARY OF THE INVENTION

Provided herein, inter alia, are tumorigenic cell lines and methods of using the same for producing cell culture and non-human animal-based model systems with increasingly aggressive tumors for evaluating the anti-neoplastic potential of candidate therapeutics.

Accordingly, in some aspects, provided herein is a T1-A cell line designated ATCC PTA-123697 or a cell line having all of the identifying characteristics of ATCC PTA-123697. In some embodiments, the cell line develops into a tumor when a cell from the cell line is injected into a non-human animal. In some embodiments, the cell line develops into a tumor when a cell from the cell line is injected into a non-human animal. In some embodiments, the tumor develops within 7-10 days of injection of the cell from the cell line into the non-human animal. In some embodiments, the cell line develops into a locally metastatic tumor when a cell from the cell line is injected into a non-human animal. In some embodiments, the locally metastatic tumor develops within 13 days of injection of the cell from the cell line into the non-human animal.

In other aspects, provided herein is a T2-A cell line designated ATCC PTA-123698 or a cell line having all of the identifying characteristics of ATCC PTA-123698. In some embodiments, the cell line develops into a distantly metastatic tumor in at least one organ or tissue when a cell from the cell line is injected into a non-human animal. In some embodiments, the cell line develops into a distantly metastatic tumor within 21-27 days of injection of the cell from the cell line into the non-human animal.

In further aspects, provided herein is a T3-PA cell line designated ATCC PTA-123699 or a cell line having all of the identifying characteristics of ATCC PTA-123699. In some embodiments, the cell line develops into a metastatic lung tumor when a cell from the cell line is injected into a non-human animal.

In other aspects, provided herein is a T3-HA cell line designated ATCC PTA-123513 or a cell line having all of the identifying characteristics of ATCC PTA-123513. In some embodiments, the cell line develops into a metastatic liver or lung tumor when a cell from the cell line is injected into a non-human animal.

In another aspect, provided herein is a T4-PA cell line designated ATCC PTA-123514 or a cell line having all of the identifying characteristics of ATCC PTA-123514. In some embodiments, the cell line develops into more than one distant metastatic tumors in more than one organs or extremities when a cell from the cell line is injected into a non-human animal. In some embodiments, the cell line develops into more than one distantly metastatic tumors within 21-24 days of injection of the cell from the cell line into the non-human animal. In some embodiments of any of the embodiments disclosed herein, the cell lines of the present invention are all derived from a single progenitor cell line that is transformed by transfection with an a nucleic acid encoding an HRAS gene. In some embodiments, the progenitor cell line is an NIH3T3 cell transformed with an HRAS gene.

Also provided herein, in other aspects, are one or more non-human animal(s) comprising tumorigenic cells derived from any of the cell lines disclosed herein. In some embodiments, the non-human animal is a mouse. In some embodiments, the mouse is immunocompromised. In some embodiments, the mouse is a nude NIH Swiss mouse.

In other aspects, provided herein is a method for producing a series of non-human animals with increasingly aggressive tumors, the method comprising: injecting at least one cell from the T1-A cell line disclosed herein subcutaneously into a first non-human animal, wherein the first non-human animal develops a primary tumor; injecting at least one cell from the T1-A cell line disclosed herein intravenously a second non-human animal, wherein the second non-human animal develops a locally metastatic tumor; injecting at least one cell from the T2-A cell line disclosed herein intravenously into a third non-human animal, wherein the third non-human animal develops a distantly metastatic tumor; injecting at least one cell from the T3-PA cell line disclosed herein intravenously into a fourth non-human animal, wherein the fourth non-human animal develops a metastatic lung tumor; injecting at least one cell from the T3-HA cell line disclosed herein intravenously into a fifth non-human animal, wherein the fifth non-human animal develops a metastatic liver or lung tumor; and injecting at least one cell from the T4-PA cell line disclosed herein intravenously into a sixth non-human animal, wherein the sixth non-human animal develops more than one distant metastatic tumors in more than one organs or extremities, thereby producing a series of non-human animals with increasingly aggressive tumors.

In further aspects, provided herein is a system for evaluating the anti-neoplastic potential of a candidate therapeutic agent against neoplastic cells from a specific stage of tumorigenesis comprising two or more of the non-human animals produced by any of the methods disclosed herein and one or more candidate therapeutic agents.

In another aspect, provided herein is a method for evaluating the anti-neoplastic potential of a candidate agent against neoplastic cells from a specific stage of tumorigenesis, the method comprising: contacting the agent with any of the cell lines disclosed herein or one or more of the non-human animals disclosed herein; and evaluating the anti-neoplastic potential of the candidate agent by determining the effect of said agent on neoplastic cell growth inhibition or tumor growth inhibition from a specific stage of tumorigenesis. In some embodiments, the agent is selected from the group consisting of a ribozyme, an antisense nucleic acid, a morpholino, a small inhibitory (si)RNA, a double stranded (ds)RNA, a micro (mi)RNA, a small molecule chemical compound, a non-antibody binding polypeptide, and an antibody or functional fragment thereof.

In further aspects, provided herein is a kit comprising: one or more of the cell lines of disclosed herein. In another embodiment, the kit further comprises one or more of the non-human animals disclosed herein. Each of the aspects and embodiments described herein are capable of being used together, unless excluded either explicitly or clearly from the context of the embodiment or aspect.

In still other aspects, provided herein are cell lines obtained from: transfecting ATCC CRL1658 cells with a Harvey-ras oncogene (HRAS) to form a transformed parent cell population; injecting the transformed parent cell population into a mouse, wherein the transformed parent cell population forms a tumor; excising the resultant tumor; culturing the cells of the excised tumor; injecting the cultured cells of the excised tumor into a second mouse; excising tumor from the second mouse; and culturing the cells of the tumor of the second mouse. In some embodiments, the mouse is an NIH Swiss mouse. In some embodiments of any of the embodiments disclosed herein, the injection is into the hindquarter. In some embodiments of any of the embodiments disclosed herein, the second mouse is a nude NIH Swiss mouse. In some embodiments of any of the embodiments disclosed herein, the injection is into the tail vein of the second mouse. In some embodiments of any of the embodiments disclosed herein, the embodiment further comprises injecting the cultured cells of the excised tumor into a third mouse; excising a locally metastatic tumor from the third mouse; and culturing the cells of the locally metastatic tumor of the third mouse. In some embodiments, the embodiment further comprises injecting the cultured cells of the locally metastatic lesion into a fourth mouse; excising a metastatic lung or liver tumor from the fourth mouse; and culturing the cells of the metastatic lung or liver tumor of the fourth mouse. In some embodiments, the embodiment further comprises injecting the cultured cells of the locally metastatic lesion into a fifth mouse; excising a distantly metastatic tumor from the fifth mouse; and culturing the cells of the distantly metastatic tumor of the fifth mouse.

BRIEF DESCRIPTION OF THE DRAWINGS

The patent application file contains at least one drawing executed in color. Copies of this patent or patent application publication with color drawing(s) will be provided by the Office upon request and payment of the necessary fee.

FIG. 2A-FIG. 2N show photomicrographs of normal and transformed cells. FIG. 2A and FIG. 2B show NIH Swiss embryonic 100×, lower and higher cell densities, respectively. FIG. 2C and FIG. 2D show NIH/3T3 100×, lower and higher cell densities, respectively. FIG. 2E and FIG. 2F show GhrasT-NIH/3T3 100×, lower and higher cell densities, respectively. FIG. 2G and FIG. 2H show T1-A 100×, lower and higher cell densities, respectively. FIG. 2I and FIG. 2J show T2-A 100×, lower and higher cell densities, respectively. FIG. 2K and FIG. 2L show T3-HA 100×, lower and higher cell densities, respectively. FIG. 2M and FIG. 2N show T4-PA 100×, lower and higher cell densities, respectively.

FIG. 3 shows detection of mouse and human ras genes by PCR analysis. Agarose gel electrophoresis of mouse and human HRAS PCR products: total DNA was isolated from NIH/3T3, T-2A and T4-PA cell lines and mouse liver. Human placenta DNA was purchased commercially. PCR Reactions were performed using human primer set (HN- 3630 with HT-4781) or mouse primer set (MN-1121 with MT-1336) on each DNA sample. Products were analyzed by agarose gel electrophoresis and portions of each gel photograph are shown at the human 1152 bp and mouse 216 bp size regions detected in ethidium bromide stained slab gels. Lanes 1, 2, 5, 6, 9, 10, 13, 14, 17 and 18 show results from the mouse primer set and lanes 3, 4, 7, 8, 11, 12, 15, 16, 19 and 20 show results from the human primer set. No products appeared in controls with each primer set without added DNA (not shown). M¼ primer set, H¼ Human primer set.

DETAILED DESCRIPTION OF THE INVENTION

The human transforming HRAS gene cloned from either the T24 or EJ bladder carcinoma cell lines is well known to transform the immortal NIH/3T3 cell line [21]. The ras oncogenes (HRAS, KRAS and NRAS) are known to exploit their signaling pathways to help drive tumorigenesis in a large number of cancer types [26]. The transforming DNA from the EJ human bladder carcinoma cell line (EJ-Ha-ras) was identified as the activated HRAS oncogene. The EJ-6-2-Bam-6a cell line (ATTC CRL-1888) was established by transfection of this activated HRAS oncogene into immortalized NIH/3T3 cells. This transfected cell line, paired with the untransfected NIH/3T3 cell line, is being used globally to evaluate the effects of HRAS transformation in the tumorigenic process. They are being used for many recent approaches to understand the control of cell death in the malignant cell [13], and to evaluate the mechanisms cancer cells utilize to alter their metabolism [15]. They have also been employed to devise ways to target cancer cells with specific decorated nanoparticles to image and ultimately kill cancer cells when the particles are attached to tumor-specific toxins [24].

Figure 1:
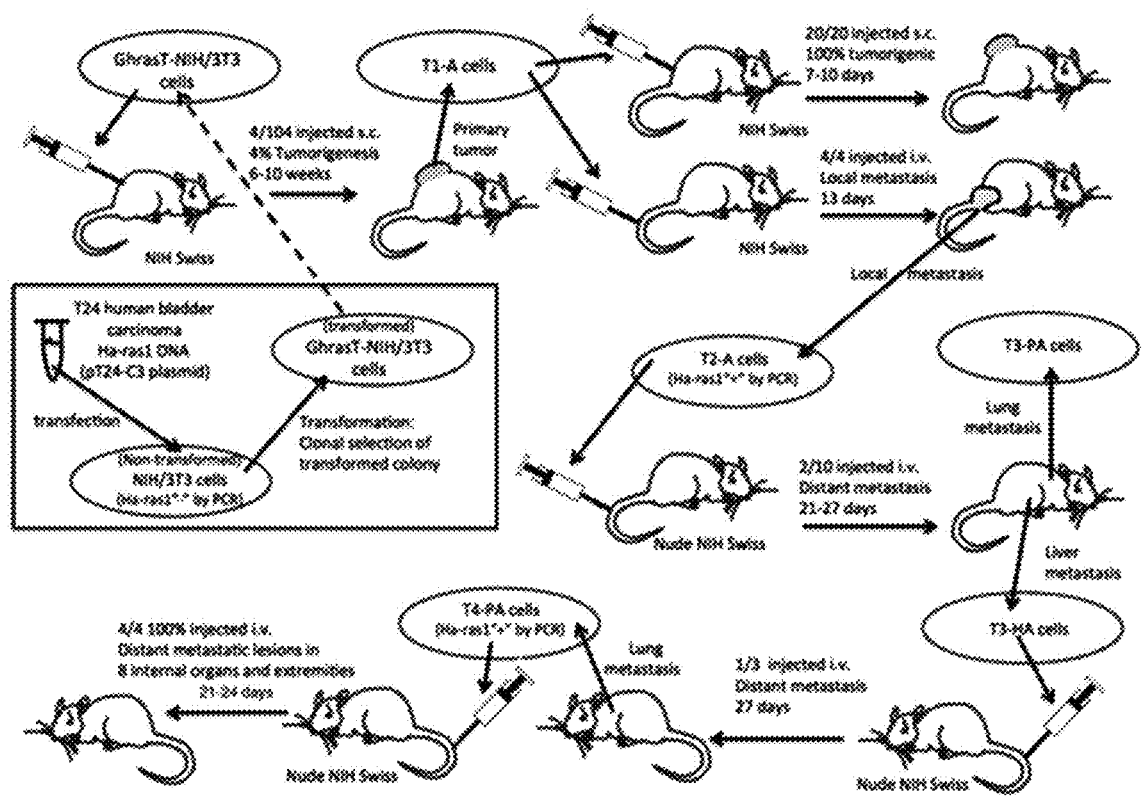
FIG. 1 is a schematic overview of a method of producing cell lines of the present invention.

The present application provides a series of cell lines established from an HRAS transfection system using T24 human bladder carcinoma DNA as well as use of the cell lines to generate non-human animal-based systems and models for evaluating the anti-neoplastic potential of candidate therapeutics. The inventors of the present invention used a novel serially extended in vivo/in vitro approach and HRAS transfected NIH/3T3 cells to derive a series of increasingly aggressive tumorigenic cell lines representative of the various stages in tumor progression and which include several additional metastatic cell types (FIG. 1, graphical abstract). The advantage of the cell lines and model systems disclosed herein lies in the fact that all transformed cell lines in the series are derived from a common transfected parent cell population, namely, a transformed GhrasT-NIH/3T3 cell line, which was generated by transfection of a non-transformed NIH/3T3 cell line with DNA from the T24 human bladder carcinoma.

The first cell line in the series (T1-A) was cultured from a primary tumor in a NIH/Swiss mouse injected subcutaneously with the GhrasT-NIH/3T3 cells. The second cell line (T-2A) was cultured from a subsequent secondary local metastasis in a NIH/Swiss mouse injected intravenously with T1-A cells. The third cell line (T3-HA) was cultured from a tertiary liver metastatic tumor in a nude NIH/Swiss mouse injected intravenously with T2-A cells. The fourth cell line (T4-PA) was cultured from a quaternary metastatic tumor in a nude NIH/Swiss mouse injected intravenously with T3-HA cells. These T4-PA cells caused wide spread metastases following intravenous injection into nude mice.

Accordingly, the cell lines and non-human animal-based in vivo/in vitro model systems disclosed herein represent a unique tool for evaluating the therapeutic potential of candidate anti-neoplastic drugs against a series of increasingly aggressive tumorigenic cells and lesions derived from a single progenitor population. Furthermore, the cell lines described herein offer the opportunity to evaluate single cell variations within and among a variety of cell lines serially derived from a common tumorigenic event(s). Consequently, the cell lines of the present invention may be used to provide insights into potential stochastic chromosomal rearrangements, eukaryotic-phenotypic, genetic, epigenetic, and metabolic network changes that have occurred within the progression leading from localized tumors to highly metastatic and invasive cells.

I. General References

The practice of the present invention will employ, unless otherwise indicated, conventional techniques of molecular biology, microbiology, cell biology, biochemistry, nucleic acid chemistry, and immunology, and mouse breeding and genetics which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons, Inc., New York, 2000, (including supplements through 2014).

II. Definitions

"Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth. In some embodiments, neoplastic cells are tumor cells or cancer cells (such as metastatic cancer cells).

The term "anti-neoplastic" as used herein is intended to encompass both destruction/killing/lysis of neoplastic cells as well as preventing their growth and/or replication. It refers to the ability to inhibit or prevent the development or spread of a neoplasm, and to limit, suspend, terminate, or otherwise control the maturation and proliferation of cells in a neoplasm. Thus, the activity of an "anti-neoplastic agent," can be tumoricidal or tumoristatic in nature.

As used herein, "tumorigenic" means an ability to form a tumor in a host non-human animal (such as a rodent, for example, a mouse). "Tumorigenesis" is understood as the production of a new tumor or tumors; or the process involved in the production of a new tumor or tumors. Tumorigenesis as used herein includes both the generation of tumors de novo from neoplastic cells and/or the generation of metastatic tumors from an established tumor.

"Metastasis," as used herein, is understood as the propagation of neoplastic cells from the organ or tumor where they originated to a different organ or tissue. It generally occurs through the blood or lymphatic system. When the neoplastic cells spread and form a new tumor, the latter is called a secondary or metastatic tumor. As used herein, the term "metastatic lesion" refers to a tumor cell introduced into the blood system that escapes the circulation to initiate or form a tumor.

As used herein, "primary tumor" refers to a tumor that develops at the site of subcutaneous injection of neoplastic cells in a non-human animal (such as a rodent) and also includes the site of occurrence of a spontaneous natural-occurring tumor. When neoplastic cells from a primary tumor spread and form a new tumor, the latter is called a "secondary" or "metastatic tumor."

"Locally metastatic," as used herein, refers to a metastatic tumor that forms near a primary tumor and is derived from the primary tumor. It also refers to a tumor that may occur near the site of a primary tumor after the primary tumor has been surgically removed and is derived from the original tumor. In some embodiments, a locally metastatic tumor is formed from cells that have migrated a short distance from the site of intravenous injection before escaping the blood circulation and forming a tumor near the site of the primary tumor.

"Distantly metastatic," as used herein, refers to a metastatic tumor that forms a significant distance from the site of the primary tumor and is derived from the primary tumor. In some embodiments, a metastatic tumor is formed from cells that have migrated a significant distance from the site of intravenous injection before escaping the blood circulation and forming a distant tumor (such as a tumor located in a different organ or tissue compared to the location of the primary tumor).

"Transformed," as used herein, refers to a cell that was changed from a normal cell to a malignant cell that is capable of producing a cancerous tumor. It can also produce a growth in soft agar when cultured in vitro. Transformed cells have lost the property of contact-inhibited growth in vitro when grown in cell culture dishes. A transformed cell will grow in multi-layers in cell culture dishes, are immortal, and can divide indefinitely. In some embodiments, the GhrasT-NIH/3T3, T1-A, T-2A, T3-PA, T3-HA, and T3-PA cells disclosed herein are all transformed. It is understood that aspects and embodiments of the invention described herein include "consisting of" and "consisting essentially of" aspects and embodiments.

Reference to "about" a value or parameter herein includes (and describes) variations that are directed to that value or parameter per se. For example, description referring to "about X" includes description of "X."

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Compositions

Provided herein is a series of tumorigenic cell lines wherein cells from each cell line in the series are capable of developing into increasingly aggressive tumors when injected into a non-human animal. The table below lists the claimed cell line designations and their corresponding deposit dates.

| Cell line Designation | ATCC Deposit Designation | ATTC Deposit Date |
|---|---|---|
| T1-A | PTA-123697 | 26 Apr. 2017 |
| T2-A | PTA-123698 | 12 Apr. 2017 |
| T3-PA | PTA-123699 | 5 Apr. 2017 |
| T3-HA | PTA-123513 | 12 Oct. 2016 |
| T4-PA | PTA-123514 | 19 Oct. 2016 |

The cell lines were deposited and will be made available to the public without restriction, but subject to patent rights, with the American Type Culture Collection (ATCC), 10801 University Boulevard, Manassas, Va., 20110. The claimed cell lines were deposited on behalf of Grove City College. These deposits were made and will be maintained in accordance with, and under the terms of, the Budapest Treaty with respect to cell line deposits for the purposes of patent procedure. These deposits will be maintained without restriction at the ATCC depository, which is a public depository, for a period of 30 years, or five years after the most recent request, or for the effective life of the patent, whichever is longer, and will be replaced if they become nonviable during that period.

A. Cell Lines

As described in Example 1 and as illustrated in FIG. 1, the cell lines of the present invention were all generated from a progenitor GhrasT-NIH/Swiss cell line that itself was produced from transformation of NIH/3T3 cells by transfection with HRAS oncogene DNA from the T24 human bladder carcinoma. These GhrasT-NIH/Swiss cells were injected subcutaneously into NIH/Swiss mice to produce primary tumors from which one was used to establish the T1-A cell line. T1-A cells injected intravenously into the tail vein of a NIH/Swiss mouse produced a local metastatic tumor near the base of the tail from which the T2-A cell line was established. T2-A cells injected intravenously into the tail vein of a nude NIH/Swiss mouse produced metastases in the liver and lung of that mouse from which the T3-HA (H=hepatic) and T3-PA (P=pulmonary) cell lines were developed, respectively. T3-HA cells injected intravenously into the tail vein of a nude mouse produced a metastasis in the lung from which the T4-PA cell line was established.

1. T1-A Cells

Provided herein are transformed T1-A cells which were derived from the transformed GhrasT-NIH/Swiss cell line which was transformed by transfection of non-transformed NIH/3T3 cells with HRAS oncogene DNA from the T24 human bladder carcinoma. Specifically, T1-A cells are derived from a primary tumor caused by injection of the progenitor GhrasT-NIH/Swiss cell line and are themselves less tumorigenic than the T1-A cells. In some embodiments, T1-A cells can be used to generate primary tumors in non-human animals by injecting them subcutaneously into the non-human animals. In such instances, about 85% to about 100%, such as any of about 85%, 86%, 87%, 88%, 89%, 90%, 91%, 92%, 93%, 94%, 95%, 96%, 97%, 98%, 99%, or 100% of animals injected subcutaneously with T1-A cells develop primary tumors. In some embodiments, the non-human animals develop primary tumors within about 7-10 days following injection, such as any of about 7, 8, 9, or 10 days following injection. In some embodiments, the non-human animal is a rodent, such as a mouse or a rat. In other embodiments, the non-human animal is a mouse, such as an immunocompromised mouse or a non-immunocompromised mouse. In other embodiments, T1-A cells can be used in vitro as a model for assaying the anti-neoplastic properties of candidate therapeutics against cancer cells that form primary tumors, but which have not yet acquired metastatic potential. In further embodiments, T1-A cells exhibit a doubling time of about 17.5 hours in vitro.

In other embodiments, T1-A cells can be used to generate locally metastatic tumors in non-human animals by injecting them intravenously into non-human animals. In such instances, about 85% to about 100%, such as any of about 85%, 86%, 87%, 88%, 89%, 90%, 91%, 92%, 93%, 94%, 95%, 96%, 97%, 98%, 99%, or 100% of animals injected intravenously with T1-A cells develop locally metastatic tumors. In some embodiments, the non-human animals develop primary tumors within about 12-14 days following injection, such as any of about 12, 13, or 14 days following injection. In some embodiments, the non-human animal is a rodent, such as a mouse or a rat. In other embodiments, the non-human animal is a mouse, such as an immunocompromised mouse or a non-immunocompromised mouse. In other embodiments, T1-A cells can be used in vitro as a model for assaying the anti-neoplastic properties of candidate therapeutics against cancer cells that form locally metastatic tumors but which have not yet acquired distantly metastatic potential.

In some embodiments, T1-A cells are cells from ATCC deposit number PTA-123697, or cells having all of the identifying characteristics of ATCC deposit number PTA-123697.

2. T2-A Cells

T2-A cells were derived from tumors produced in immunocompromised mice by injecting them intravenously with locally metastatic T1-A cells. In some embodiments, T2-A cells can be used to generate locally metastatic or distantly metastatic tumors in at least one organ or tissue in non-human animals by injecting them intravenously into the non-human animals. For example, non-human animals injected with T2-A cells can develop tumors in one or more of the liver, lung, pericardium, or throat. About 50% to about 100%, 60% to about 100%, about 70% to about 100%, about 80% to about 100%, about 90% to about 100% such as any of about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of animals injected intravenously with T2-A cells develop locally metastatic or distantly metastatic tumors. In some embodiments, the non-human animal is a rodent, such as a mouse or a rat. In other embodiments, the non-human animal is a mouse, such as an immunocompromised mouse or a non-immunocompromised mouse. In other embodiments, T2-A cells can be used in vitro as a model for assaying the anti-neoplastic properties of candidate therapeutics against cancer cells that have progressed passed the primary tumor or locally metastatic stage and which have become at least partly metastatic. In further embodiments, T2-A cells exhibit a doubling time of about 15.5 hours.

In some embodiments, T2-A cells are cells from ATCC deposit number PTA-123698, or cells having all of the identifying characteristics of ATCC deposit number PTA-123698.

3. T3-PA Cells

T3-PA cells were derived from tumors produced in immunocompromised mice by injecting them intravenously with metastatic T2-A cells that had formed tumors in the lungs. In some embodiments, T3-PA cells can be used to generate metastatic lung tumors in non-human animals. About 50% to about 100%, 60% to about 100%, about 70% to about 100%, about 80% to about 100%, about 90% to about 100% such as any of about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of non-human animals injected intravenously with T3-PA cells develop lung tumors. In some embodiments, the non-human animal is a rodent, such as a mouse or a rat. In other embodiments, the non-human animal is a mouse, such as an immunocompromised mouse or a non-immunocompromised mouse. In other embodiments, T3-PA cells can be used in vitro as a model for assaying the anti-neoplastic properties of candidate therapeutics for cancer cells that have progressed into a stage corresponding to metastatic tumors localized in the lung.

In some embodiments, T3-PA cells are cells from ATCC deposit number PTA-123699, or cells having all of the identifying characteristics of ATCC deposit number PTA-123699.

4. T3-HA Cells

T3-HA (H=hepatic) cells were derived from a metastatic tumor formed in the liver of an immunocompromised mouse injected intravenously with metastatic T2-A cells that had formed tumors in the liver. In some embodiments, T3-HA cells can be used to generate metastatic lung and liver tumors in non-human animals. About 50% to about 100%, 60% to about 100%, about 70% to about 100%, about 80% to about 100%, about 90% to about 100% such as any of about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of non-human animals injected intravenously with T3-PA cells develop liver and lung tumors. In some embodiments, the non-human animal is a rodent, such as a mouse or a rat. In other embodiments, the non-human animal is a mouse, such as an immunocompromised mouse or a non-immunocompromised mouse. In other embodiments, T3-HA cells can be used in vitro as a model for assaying the anti-neoplastic properties of candidate therapeutics against cancer cells that have progressed into a stage corresponding to metastatic tumors localized in the liver. In further embodiments, T3-HA cells exhibit a doubling time of about 17.5 hours.

In some embodiments, T3-HA cells are cells from ATCC deposit number PTA-123513, or cells having all of the identifying characteristics of ATCC deposit number PTA-123513.

5. T4-PA Cells

T4-PA cells were derived from tumors produced in immunocompromised mice by injecting them intravenously with T3-HA cells that had formed tumors in the liver. In some embodiments, T4-PA cells can be used to generate metastatic tumors in non-human animals to more than one location (other than the liver), such as, without limitation, the liver, neck, lungs, intestines, legs, and in the groin and pancreas areas. In some embodiments, T4-PA cells can be used to generate primary tumors in non-human animals by injecting them subcutaneously into the non-human animals. In some embodiments, T4-PA cells can be used to generate locally metastatic and metastatic tumors in non-human animals by injecting them intravenously into the non-human animals. In such instances, about 85% to about 100%, such as any of about 85%, 86%, 87%, 88%, 89%, 90%, 91%, 92%, 93%, 94%, 95%, 96%, 97%, 98%, 99%, or 100% of animals injected intravenously with T4-PA cells develop multiple (such as 2, 3, 4, 5 or 6) metastatic tumors. In some embodiments, the non-human animal is a rodent, such as a mouse or a rat. In other embodiments, the non-human animal is a mouse, such as an immunocompromised mouse or a non-immunocompromised mouse. In other embodiments, T4-PA cells can be used in vitro as a model for assaying the anti-neoplastic properties of candidate therapeutics against cancer cells that have progressed into a highly metastatic stage. In further embodiments, T4-PA cells exhibit a doubling time of about 18.5 hours.

In some embodiments, T4-PA cells are cells from ATCC deposit number PTA-123514, or cells having all of the identifying characteristics of ATCC deposit number PTA-123514.

B. Non-Human Animals

Also provided herein are non-human animals comprising any of the cells or cell lines disclosed herein (such as T1-A, T2-A, T3-PA, T3-HA, or T4-PA cells). Such non-human animals can be used as model systems, alone or in series (such as, for example, wherein one or more animals comprises T1-A cells, one or more animals comprises T2-A cells, one or more animals comprises T3-PA cells, etc.), in order to evaluate the anti-neoplastic potential of a candidate agent against neoplastic cells from a specific stage of tumorigenesis.

The term "non-human animal" refers to any animal other than a human. Examples of non-human animals include, without limitation, aquatic animals (e.g., fish, sharks, dolphin, and the like), farm animals (e.g., pigs, goats, sheep, cows, horses, rabbits, and the like), rodents (e.g., rats, guinea pigs, and mice), non-human primates (e.g., baboon, monkeys, and chimpanzees), and domestic animals (e.g., dogs and cats). The non-human animals provided herein can be immunocompromised or immunodeficient. For example, a non-human animal can be a severe combined immunodeficiency (SCID) animal, such as a mouse (e.g., an X-linked SCID or a RAG1$^{-/-}$ or RAG2$^{-/-}$ mouse).

Methods for generating non-human animals comprising any of the cells of the present invention are well known in the art, particularly for rodent model organisms such as mice and rats. Cells can be introduced into the animal by any means known in the art such as, without limitation, by intravenous administration, subcutaneous administration, or by graft.

IV. Methods of the Invention

Also provided herein are methods for evaluating the anti-neoplastic potential of a candidate agent against neoplastic cells from a specific stage of tumorigenesis. The method involves contacting one or more of the cells described herein (such as one or more of a T1-A, T2-A, T3-PA, T3-HA, or T4-PA cells) with a candidate anti-neoplastic therapeutic agent and evaluating the anti-neoplastic potential of the candidate agent by determining the effect of the candidate therapeutic agent on neoplastic cell growth inhibition and/or tumor growth inhibition on a specific stage of tumorigenesis (such one or more of a primary tumor, a locally metastatic tumor, a lung or liver metastatic tumor, or a highly aggressive distant metastatic tumor). In some embodiments, the cells can be present in a non-human animal (such as a rodent, for example, a mouse) that has been injected with the cells in order to form a tumor or tumorigenic lesion. Cell culture is routine and can be accomplished via any method known in the art.

Accordingly, "contacting" used herein includes physically contacting any of the cells disclosed herein or non-human animals that have neoplasms or tumors caused by any of the cells disclosed herein with a candidate therapeutic agent or introducing (for example by injecting or via ingestion) the compound into the non-human animals. In some embodiments, the cells are contained in an aqueous medium in a microtiter well, such as in a multi-well plate, e.g., a 96-well plate. In some embodiments, the candidate therapeutic agents are administered to the cells or to the non-human animals by electroporation, lipofection, or ingestion or by using bolistic cell loading technology in which particles coated with the candidate therapeutic agent are introduced into the cell or tissue of interest as a bolus using a high-pressure gun. The cells of the present invention may be pretreated prior to exposure to the candidate therapeutic agent, for example to facilitate the penetration and/or contacting of the candidate therapeutic agent.

In some embodiments, the candidate therapeutic agent is administered to the cells by dissolving the candidate therapeutic agent in media containing the cells. Alternatively, the candidate therapeutic agent may first be dissolved in the medium and the cells submerged in the media subsequently. In some embodiments, the candidate therapeutic agent is administered to the cells by microinjecting the candidate therapeutic agent into the cells. The candidate therapeutic agent may be brought into contact with the cells of the present invention alone, in conjunction with a variety of solvents (e.g., dimethylsulfoxide (DMSO) or the like) or carriers (including, e.g., peptide, lipid or solvent carriers), or in conjunction with other compounds. In some embodiments, contacting comprises injecting said candidate therapeutic agent into the non-human animals comprising any of the cells disclosed herein. Suitable vehicles for injection include, but are not limited to, E3 buffer and DMSO.

As used herein, the phrase "cell growth inhibition" or "tumor growth inhibition" means a reduction or cessation of the growth of a neoplastic cell or a reduction or cessation in the growth of a tumor. Cell growth inhibition can be determined using any means known in the art. In some embodiments, cells undergoing growth inhibition exhibit one or more signs of apoptosis (such as, but not limited to, membrane blebbing, annexin V staining, DNA fragmentation, caspase activation, or any other marker of programmed cell death known in the art). In other embodiments, tumor growth inhibition can be determined by observing a reduction in the size of the tumor, for example, by using a caliper or by ascertaining the weight of an excised tumor.

Candidate anti-neoplastic agents for use in the methods of the present invention can be an antibody or a non-antibody polypeptide. Additionally, the agent can be an inhibitory nucleic acid, such as an antisense oligonucleotide or a siRNA. Further, the agent can also be a small molecule chemical compound.

A. Antibodies

In some aspects, the candidate anti-neoplastic agent is an antibody. Antibodies are proteins that bind, preferably specifically, to other proteins, nucleic acids, lipids, or any other antigen. Variants of antibodies can be made based on information known in the art, without substantially affecting the activity of antibody. For example, antibody variants can have at least one amino acid residue in the antibody molecule replaced by a different residue. Fragments of antibodies may also be used (such as, but not limited to, Fv, Fab, Fab', or F(ab)$_2$ fragments), as well as genetically-engineered antibodies or antigen binding fragments thereof, including single chain antibodies, humanized antibodies, antibodies that can bind to more than one epitope (e.g., bi-specific antibodies), or antibodies that can bind to one or more different antigens (e.g., bi- or multi-specific antibodies), may also be employed. For antibodies, the sites of greatest interest for substitutional mutagenesis generally include the hypervariable regions, but framework region (FR) alterations are also contemplated. For antibodies, one type of substitutional variant involves substituting one or more hypervariable region residues of a parent antibody (e.g. a humanized or human antibody). Generally, the resulting variant(s) selected for further development will have improved biological properties (e.g., affinity) relative to the parent antibody from which they are generated.

A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

B. Non-Antibody Binding Polypeptides

In some aspects, the candidate anti-neoplastic agent is a non-antibody binding polypeptide. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al., (1990) *Proc. Natl. Acad. Sci. USA*, 87:6378; Lowman, H. B. et al., (1991) Biochemistry, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363, and Smith, G. P. (1991) *Current Opin. Biotechnol.*, 2:668).

C. Small Molecule Chemical Compounds

In some aspects, the candidate anti-neoplastic agent is a small molecule chemical compound. Small molecules can be molecules other than binding polypeptides or antibodies as defined herein. Small molecules may be identified and chemically synthesized using known methodology (see, e.g., International Patent Application Publication Nos. WO00/00823 and WO00/39585). Small molecules are usually less than about 2000 Daltons in size or alternatively less than about 1500, 750, 500, 250 or 200 Daltons in size. In this regard, it is noted that techniques for screening small molecule libraries for molecules that are capable of binding to a polypeptide target are well known in the art (see, e.g., PCT Publication Nos. WO00/00823 and WO00/39585). Small molecules may be, for example, aldehydes, epoxides, or fluoro methyl ketones.

The small molecule chemical compound may be a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule or mediating a biological activity of interest (such as, but not limited to, inhibition of cellular proliferation or tumor cell growth). Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

D. Inhibitory Nucleic Acids

In another aspect, the candidate anti-neoplastic agent is one or more inhibitory nucleic acid(s). The inhibitory nucleic acid can be, without limitation, any of an RNA interference agent, such as any of those disclosed herein (for example, an antisense oligonucleotide, a siRNA, a dsRNA, or a ribozyme). While preferred, absolute complementarity of an inhibitory nucleic acid to a target is not required. As used herein, an inhibitory nucleic acid sequence is "complementary" to a target nucleic acid when the inhibitory nucleic acid has a sequence sufficiently complementary to be able to hybridize with the target, thereby forming a stable duplex. The ability to hybridize will depend on both the degree of complementarity and the length of the oligonucleotide. Generally, the longer the hybridizing inhibitory nucleic acid, the more base mismatches with a given target it may contain and still form a stable duplex. A person having ordinary skill in the art can ascertain a tolerable degree of mismatch by use of standard procedures to determine the melting point of the hybridized complex.

Inhibitory nucleic acids can include one or more alternate internucleoside linkages, such as, but not limited to, phosphorothioate (Mag at al., *Nucleic Acids Res.* 19: 1437-1441, 1991; and U.S. Pat. No. 5,644,048),peptide nucleic acid or PNA (Egholm, *Nature*, 3685:566-568, 1993; and U.S. Pat. No. 6,656,687), phosphoramide (Beaucage, *Methods Mol. Biol.* 20:33-61, 1993), phosphorodithioate (Capaldi et al., *Nucleic Acids Res.*, 28:E40, 2000). Other oligonucleotide analogs include, but are not limited to, morpholino (Summerton, *Biochim. Biophys. Acta*, 1489: 141-158, 1999), locked oligonucleotides (Wahlestedt wt al., *Proc. Natl. Acad. Sci. USA*, 97:5633-5638, 2000), peptidic nucleic adds or PNA (Nielsen et al., 1993; Hyrup and Nielsen, 1996) or 2-o-(2-methoxy)ethyl modified 5' and 3' end oligonucleotides (McKay et al., *Biol. Chem.*, 274: 1715-1722, 1999). All of the preceding publications are hereby expressly incorporated by reference.

Further, any of the inhibitory nucleic acids disclosed herein may additionally contain any combination of deoxyribo- and/or ribonucleotides, as well as any combination of natural and/or synthetic bases, including uracil, adenine, thymine, cytosine, guanine, inosine, xathanine hypoxathanine, isocytosine, isoguanine, etc.

The inhibitory nucleic acids discussed herein can include one or more modified base moiety such as, but not limited to, 5-fluorouracil, 5-bromouracil, 5-chlorouracil, 5-Iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxy acetic acid methylester, uracil-5-oxyacetic acid (v), 5-methyl-2-thiouracil, 3-(3-amino-3-N2-carboxypropyl)uracil, (acp3)w, and/or 2,6-diaminopurine.

Inhibitory nucleic acids contemplated within the scope of the present invention can also have one or more modified sugar moiety such as, but not limited to, arabinose, 2-fluoroarabinose, xylulose, and hexose. The inhibitory nucleic acids of the present invention should be at least ten nucleotides in length, and may range from 10 to about 50 nucleotides in length, such as 15, 20, 30, 35, 40, 45, or 50 nucleotides in length, inclusive, including any values falling in between these numbers.

IV. Systems and Kits

Additionally provided herein are systems for evaluating the anti-neoplastic potential of a candidate agent against neoplastic cells from a specific stage of tumorigenesis. The system comprises a) cells from at least two (such as any of about 2, 3, 4, or 5) of the cell lines disclosed herein, with each cell line representative of a specific stage of tumorigenesis; and b) one or more candidate anti-neoplastic agents. In a further embodiment, the system comprises two or more non-human animals (such as any of about 2, 3, 4, or 5), wherein each animal has been injected with one of the cell lines disclosed herein, with each cell line representative of a specific stage of tumorigenesis and one or more candidate anti-neoplastic agents.

The invention further comprises kits containing one or more of the cell lines disclosed herein (such as one or more of a T1-A, T2-A, T3-PA, T3-HA, or T4-PA cells). Alternatively, the kits may contain additional items for culturing the cells, such as, without limitation, cell culture plates, cell culture media, and written instructions for culturing the cells and using the same to investigate the anti-neoplastic potential of candidate therapeutic agents. The kit may further include one or more of the non-human animals disclosed herein (such as a rodent, for example, a mouse). In some embodiments, the non-human animal is immunocompromised.

The invention can be further understood by reference to the following examples, which are provided by way of illustration and are not in any way meant to be limiting.

EXAMPLES

Example 1

Materials and Methods

Animals. Breeding pairs of NIH Swiss and NFS/NCr mice were obtained from L. Watson at NIH or the Jackson Labs and bred as outbred or inbred strains, respectively, as described by the Jackson Lab protocols. All mice at the Oral Roberts University Medical School were housed in the animal facility of the Biomedical Research Center, fully accredited by the American Association for the Accreditation of Laboratory Animal Care, and cared for in accordance with the guidelines of the National Research Council for the care and use of laboratory animals under the supervision of a licensed veterinarian. All mice at Grove City College were cared for with the same animal studies guidelines for animal use as approved by the Grove City College Institutional Review Board, which served as the animal oversight committee at the time. Nude mice (Nu-/Nu-) were obtained from Jackson Labs, Farmington, Conn. (common name: nu/nu; strain name: NU/J; stock number: 002019) or obtained from a breeding pair (Nuþ/Nu-) offspring. These are from a spontaneous mutation athymic (nude) inbred mice on an N:NIH (s) background homozygous for nude marker, Nu-/N- and immunocompromised. The two main defects of mice homozygous for the nude spontaneous mutation (Foxn1nu, formerly Hfh11nu) are abnormal hair growth and defective development of the thymic epithelium. The Jackson Laboratory imported the nude mutation from the NIH on an outbred stock. As of 2008, the strain has been inbred for at least 100 generations. The studies reported here with these mice were completed between 1995 and 2000. NFS/NCr inbred mice were obtained from the Jackson Lab and maintained as an inbred colony. They have a very low incidence of spontaneous lymphoma.

Source, Derivation and Growth Characteristics of Each Cell or Cell Line (FIG. 1). All cells and cell lines were grown at 37° C. in 5% $CO_2$/95% air in Dulbecco's modified Eagle's medium (DMEM) (catalogue #12320-032, GIBCO, Grand Island, N.Y.) supplemented with extra added D- (þ) glucose (catalogue #G-5400, Sigma Chemical Company, St. Louis, Mo.) (4.5 g/L), 10% fetal calf serum (catalogue #SH30070.02, Hyclone Laboratories, Logan, Utah), and 20 Units/ml penicillin, and 20 µg/ml streptomycin (catalogue #15140-122, Sigma Chemical Company). Extra glucose was included to insure a rich glucose source for rapidly growing tumor cells that are known to utilize aerobic glycolysis as a major source of energy and glycolytic intermediates [39,41].

Normal Primary NIH Swiss Embryonic Cell Cultures (Mortal).These cells were prepared from 17 to 19 days old NIH Swiss mouse embryos by fine mincing of whole embryos with scissors by the methods employed by Todaro and Green [37]. These minces were used for growing primary normal cell cultures and for DNA extractions as needed. The tissue was disaggregated with 0.25% trypsin-EDTA (catalogue #25200-056, GIBCO), cells were collected by centrifugation, resuspended in saline (0.9% NaCl) (catalogue #R5200-01, B. Braum Medical, Inc., Irvine Calif.) and when useful, viable cells were identified by Trypan blue exclusion (catalogue #15250061, GIBCO), and counted in a hemocytometer. Cells were plated at $4.3 \times 10^5$ cells/60 mm diameter dishes and grown in D-MEM supplemented as described above. Cultures were expanded and subcultures were frozen in Recovery Cell Culture Freezing Media (catalogue #12648-010, GIBCO) and stored in liquid nitrogen tanks as stocks.

NIH/3T3 Cells (Immortal). The "immortal" NIH/3T3 cells (ATCCs CRL1658™) cells were purchased from the American Type Culture Collection (Manassas, Va.) at passage #126. These cells were originally developed [10] by growing primary embryonic cells, prepared as described above [37], using a rigid transfer schedule (every 3-4 days). These cells were non-tumorigenic when $1 \times 10^6$ cells were injected s.c. into 23 NFS/Ncr inbred mice or 105 outbred NIH Swiss mice (Table 1). Cultures were expanded and subcultures were frozen and stored in liquid nitrogen as stocks.

TABLE 1

Primary tumor occurances in mice injected with various cell lines[a].

| Cell line | Recipient mouse | Injection size | # Of tumors per # of mice injected | % Tumors | Time period |
|---|---|---|---|---|---|
| NIH/3T3 | NFS/NCr (inbred) | Hind quarter | 0/23 | 0 | |
| NIH/3T3 | NIH Swiss (outbread) | Hind quarter | 0/105 | 0 | |
| GhrasT-NIH/3T3 | NFS/NCr (inbred) | Hind quarter | 14/45 | 31 | 6-10 weeks |
| GhrasT-NIH/3T3 | NIH Swiss (outbread) | Hind quarter | 4/104 | 4 | 6-10 weeks |
| GhrasT-NIH/3T3 | nude NIH/Swiss | Hind quarter | 2/2 | 100 | N.A.[b] |
| T1-A | NFS/NCr (inbred) | Hind quarter | NIL[c] | | |
| T1-A | NIH Swiss (outbread) | Hind quarter | 20/20 | 100 | 7-10 days |
| T1-A | NIH Swiss (outbread) | Tail vein, i.v. | 4/4 | 100 | 13 days[d] |
| T1-C | NFS/NCr (inbred) | Hind quarter | NIL[c] | | |
| T1-C | NIH Swiss (outbread) | Hind quarter | 13/14 | 93 | 7-10 days |

[a]$10 \times 10^6$ cells injected per mouse.
[b]Not available.
[c]Not determined.
[d]These 4 tumors were local metastases in the base of the tails and the T-2A cell line was established from one of them.

Tumorigenic Ras Oncogene-Transfected NIH/3T3 Cells (Transformed).The HRAS oncogene-transfected NIH/3T3 cells were obtained from Dr. David A. Goldthwait at the Department of Biochemistry, Case Western Reserve University in Cleveland, Ohio and designated as G-hrasT-NIH/3T3 cells. (G denotes their source from the Goldthwait Lab, T denotes their transformed cell type.) The Goldthwait cells were isolated from a focus of transformed cells following transfection with DNA from the T24 Human bladder carcinoma. This cell line contains the Harvey-ras oncogene isolated from the T24 human bladder carcinoma that has been shown to have a glycine to valine substitution at the twelfth amino acid residue of the T24 oncogene encoded p21 protein [28]. The pT24-C3 plasmid (ATCC 41000™) used for the transfection of the NIH/3T3 cell line by Dr. Goldthwait is a pBR322 derived plasmid containing the 6.6 Kilo base pair BamHI fragment of the T24-Ha-ras1 oncogene and is carried in *E. coli* C-600 strain (Goldthwait, D. A., unpublished results). GhrasT-NIH/3T3 cultures were expanded and subcultures were frozen and stored in liquid nitrogen as stocks.

Highly Tumorigenic Ras T1-A Cells. Following s.c. injection of $1 \times 10^6$ GhrasT-NIH/3T3 cells/mouse into hindquarters of 104 outbred NIH Swiss mice, four mice formed single primary tumors within 6 to 10 weeks at their injection sites (Table 1). Two of these tumors from separate mice were excised, minced and cultured as described above giving rise to the T1-A and T1-C cell lines. The T1-A and T1-C cells were subcultured several times and stocks were saved frozen in liquid nitrogen. Additionally, to assess the tumorigenic potential of the T1-A and T1-C cell lines, 20 and 14 outbred NIH Swiss mice were injected s.c. in the hindquarters with T1-A ($1 \times 10^6$ cells/mouse) or T1-C ($1 \times 10^6$ cells/mouse) cells respectively and observed for tumors at the injection sites.

T2-A Cell Line from Local Metastasis in NIH Swiss Mouse. To seek a metastatic lesion derived from these T1-A cells, $1 \times 10^6$ cells were injected into the tail veins of several NIH Swiss mice. A tumor was located in the rump near the base of the tail of one mouse within 13 days of tail vein injection. This local metastasis was excised, minced and cultured, establishing the T2-A cell line. These cells were expanded and subcultures were frozen and stored in liquid nitrogen. Thus, this T2-A cell line was derived from a fast growing local metastasis close to but not at the site of injection in the tail.

T3-HA and T3-PA Metastatic Cells from Distant Liver Lung Metastasis in a Nude NIH Swiss Mouse. In attempts to acquire a highly metastatic cell line in this series, $1 \times 10^6$ T2-A cells were injected into the tail veins of four immune-compromised nude NIH/Swiss mice. One mouse was sacrificed periodically and examined for evidence of tumors. After 3.5 weeks a mouse was sacrificed which contained a metastatic lesion in both the liver and a lung that were excised, minced, cultured and designated T3-HA (H=hepatic) and T3-PA (P=pulmonary) cells, respectively. These cells were expanded in culture and stored in liquid nitrogen.

T4-PA metastatic cells from distant lung metastasis in nude NIH Swiss Mouse. To determine if the T3-HA cells derived from the first distant metastatic lesion would generate second metastatic lesions in the liver, $0.7 \times 10^6$ T3-HA cells were injected into the tail veins of four NIH/Swiss nude mice. After 4 weeks, a metastatic lesion was found in the lung of one mouse. The lesion was excised, minced, cultured and the cells were designated T4-PA (P=pulmonary) cells. These cells were expanded and stored in liquid nitrogen.

DNA Extraction. Total DNA was isolated from tissue or cell pellets by a modification of the methods of Davis et al. [5].

Human Ras Oncogene Polymerase Chain Reaction (PCR) Analysis. The presence of this human oncogene in the ras transfected G-hrasT-NIH/Swiss and its descendent cell lines was confirmed by PCR amplification with the use of human specific H-ras primers. Mouse specific primers were used for a control PCR. Primers were designed by methods similar to those of [20] as published previously [27, p. 422].

Primers Designed: HN, MN=human or mouse primer that becomes the nontemplate strand of the DNA. HT, MT=human or mouse primer that becomes the template strand of the DNA. Human ras primers: designed and named from GenBank: J00277; formerly V00574 [29,36]. These human specific primers will amplify the same region in either the normal human proto-oncogene or the human T24-Ha-ras1 oncogene.

```
HN-3630
                                       (SEQ ID NO: 1)
    5'-CTG-TCT-TCA-ACA-TCC-CAA-ATG-CC-3'

HT-4781
                                       (SEQ ID NO: 2)
    5'-AGT-GTG-GTA-TTC-CCT-GGA-CAA-AAG-G-3'
```

Mouse Ras Primers: designed and named from GenBank: Z50013.1 [25]. These mouse specific primers will amplify a region in the normal mouse proto-oncogene.

```
MN-1121
                                       (SEQ ID NO: 3)
    5'-GGC-CTT-AGT-TCT-TCT-TGT-CC-3'

MT-1336
                                       (SEQ ID NO: 4)
    5'-AAC-CAA-CAC-AAA-TAG-GGA-GC-3'
```

PCR was performed as described previously [27, p. 422]. DNA was purified as described above and purity and concentration were analyzed via UV/VIS spectrophotometry. Each 50 µL reaction contained 10 mM Tis-HCl, pH 8.3, 50 mM KCl, 1.5 mM MgCl2, 200 µM each of dATP, dCTP, dGTP, dTTP, 0.2 µM primer one (forward) and 0.2 µM primer two (reverse), ~0.5 gig DNA, 1.25 Units of Taq-Gold polymerase (Applied Biosystems, Grand Island, N.Y.). The thermocycler program included 10 min at 95° C.; a 40-cycle repeat of: 1 min at 94° C., 1 min at 55° C., and 1 min at 72° C., and followed by a polishing time of 6 min at 72° C. Agarose slab gel electrophoresis was performed and EtBr stained gels were photographed by a Gel Doc XR from BIO-RAD using Quantity Ones software (BIO-RAD, Hercules, Calif.) to analyze the gels and assign a specific base pair value to each DNA fragment based on the sizing standards.

Determination of Cell Growth Rates. Cells were plated in the DMEM described above in 60 mm diameter dishes with $2 \times 2$ mm$^2$ square grids (Corning cat #430196, Corning, N.Y.). Six predetermined squares were premarked with marking pen on each dish prior to use. The squares were scattered in such a way that each $2 \times 2$ mm$^2$ square area would be representative of the entire plate. Photographs were taken daily when cells reached 20-40% confluency (day 0) with an Olympus DP12 inverted Microscope (Olympus America, Inc., Melville, N.Y.) with a Digital Camera System at 100× in the center of each selected $2 \times 2$ mm$^2$ square. Cell counts for each square were determined from the photomicrographs and the average for the 6 squares was determined for each day. Results for each day were normalized to fold increase relative to day 0. Statistical significance was determined via T-test.

Example 2

Normal NIH Swiss Embryonic Cells

The normal primary NIH Swiss embryonic cells used to establish the other cell lines in this tumorigenic progression model were obtained from 17 to 19 days old NIH Swiss mouse embryos [37]. They are anchorage dependent, contact inhibited, and mortal, surviving about 30 cell divisions before they become senescent as typical for most diploid cell cultures [17,37].

Example 3

NIH/3T3 Cell Line

The NIH/3T3 cell line was derived from NIH Swiss embryonic cells that have escaped this senescent "crisis" to become, immortal and contact inhibited. Although not transformed, they already have obtained properties associated with transformed cells [17]. They were not tumorigenic (Table 1) in the inbred NFS/NCr mice (0 tumors in 23 mice injected) or in the outbred NIH Swiss strain of mice (0 tumors in 105 mice injected). Each mouse was injected with $1 \times 10^6$ cells s.c. This negative result with NFS/NCr mice was the same as the results of Bernstein and Weinberg [3]. Variable tumorigenic and metastatic capabilities of NIH/3T3 cells have been reported. NIH/3T3 cells produce tumors in BALB-c nude mice [8]. These cells grow rapidly and when transferred at $4.3 \times 10^5$ cells/50 mm diameter culture dish they form confluent monolayers within 2-3 days. Differences in NIH/3T3 cell stocks, passage numbers, site of tumor cell inoculation and cell number inoculations may be responsible for different outcomes. In addition, in some transfection experiments, untransfected control NIH/3T3 cells have been shown to undergo "spontaneous transformation", thought to be more frequent when these cells are maintained at confluency for extended times prior to subculturing [30,8].

Example 4

GhrasT-NIH/3T3

Transfecting the Harvey-ras oncogene into the NIH/3T3 cell line is well known to transform it into a tumorigenic cell type [3]. To confirm this, the tumorigenic capability of the ras-oncogene transfected NIH/3T3 cells (GhrasT-NIH/3T3) was tested for tumor formation in normal mice. Injection of $1 \times 10^6$ cells s.c. into the rear flank of mice produced (20-30 mm diameter) primary tumors in 14 of 45 (31%) of inbred NFS/NCr mice and in 4 of 104 (4%) of outbred NIH/Swiss mice all within 6-10 weeks (Table 1). This was different than the findings of Bernstein and Weinberg who reported 100% tumor formation when injecting equivalent amounts of the EJ-6-2-Bam-6a cells (ATCC-1888TM) into the NFS/NCr mouse strain.

Without being bound to theory, these differences may indicate that the immortalized NIH/3T3 cells transfected with the plasmid containing the T24 DNA that yielded the GhrasT-NIH/3T3 cells may have undergone a more severe chaotic genomic rearrangement during transfection than the NIH/3T3 cells transfected with the plasmid containing the EJ-6-2DNA that yielded EJ-6-2Bam-6a cell line. Since several studies have indicated significant phenotypic changes can occur with transfection with empty vectors into several cell lines [33], the role of different vectors used to produce these two cell lines and the stochastic events that occurred during each transfection process may account for some of the phenotypic differences.

Consistent with the results of Bernstein and Weinstein's EJ-6-2-Bam-6a cells' results [3], injection of these GhrasT-NIH/3T3 cells s.c. into the rear flank of two nude NIH Swiss mice produced tumors at the site of injection in each mouse (Table 1). Other studies [8] using a third ras oncogene transfected NIH/3T3 cell line, A51 [7], injected s.c. into BALB/c nude mice generated primary tumors in 15-25 days. Some of the differences between the findings with the GhrasT-NIH/3T3 cells and the EJ-6-2-Bam-6a cells could be related to the number of transfections used to produce these two cell lines or the specific site where the ras oncogene BamHI fragment inserted into the two different NIH/3T3 mouse cell genomes during each transfection process. In summary, GhrasT-NIH/3T3 cells are transformed, immortal and tumorigenic (Table 1).

Example 5

Highly Tumorigenic Ras T1-A Cell Line

Two primary tumors selected from the four observed tumors produced at the cell's injection sites following s.c. injection of GhrasT-NIH/3T3 cells into 104 outbred NIH Swiss mice were excised, minced and cultured as described above giving rise to the T1-A and T1-C cell lines. Their tumorigenic capability was tested by s. c. injection into the hindquarters of NIH Swiss mice. T1-A cells produced 20 tumors in 20 mice (100%) and T1-C produced 13 tumors in 14 mice (93%) all within 7-10 days (Table 1). This indicated the T1-A and T1-C cell lines were significantly more aggressive at producing tumors than the GhrasT-NIH/3T3 cells that required 6 to 10 weeks for tumor growth. All but one of the 34 mice injected developed a primary tumor and the tumors developed 4-10 times faster than the ras-transformed GhrasT-NIH/3T3 cells did in outbred NIH/Swiss mice (Table 1). Thus, the inherent tumorigenic capabilities of the T1-A and T-1C cells have each increased in NIH/Swiss mice as this GhrasT-NIH/3T3 tumor line was moved from cultured cells to growths in vivo. The similar highly tumorigenic phenotypes of these two cell lines originating from tumors in similar in vivo microenvironments in separate mice is consistent with the concept they each may contain some transitional or dominant CCAs they acquired from the GhrasT-T-NIH/3T3 cells that gave them similar selective growth advantages. WGS and SKY analysis of these cell lines and tumors and downstream cell lines generated from them could test this possibility. These analyses may help shed some light on what chromosomal/gene arrangements may give these cells selective tumorigenic advantages.

Example 6

T2-A Cell Line from Local Metastasis in NIH Swiss Mouse

T1-A cells ($1 \times 10^6$/mouse) were injected i.v. into the tail veins of NIH Swiss mice (Table 2). A local metastatic tumor developed in the rump near the base of the tail of one mouse within 13 days, again illustrating a more rapid tumorigenic process than the original GhrasT-NIH/3T3 cells. No distant metastatic lesions were found in the mice injected. Cells cultured from this local metastatic tumor were designed T2-A cells. Therefore, this T2-A Cell line was derived from a fast growing local metastasis close to, but not at the site of injection in the tail.

TABLE 2

Metastatic tumor occurrence in mice after tail vein injection with various cell lines.

| Cell line (passage #s) # of mice injected | Recipient | # Of mice injected | Outcomes |
|---|---|---|---|
| T1-A (n.a.)[a] | NIH Swiss (outbred) | 4 | Four had a local metastatic tumor in rumps near tails after 13 days, none with obvious internal metastatic lesions. The T2-A cell line was established from one of these local metastases. |
| T2-A (7, 9) | Nude NIH/Swiss | 10 | Four died within 21-27 days; most of the other 6 all had local mets in rump near tail; two others developed distant metastatic tumors in the liver, lung pericardium, or throat. The T3-HA cell line was established from one met in the liver. |
| T3-HA (2, 3) | Nude NIH Swiss (inbred) | 3 | One died after 58 days, one had no mets after 34 days and one had metastatic tumors in the liver and lung after 27 days. T4-PA cell line was established from this lung. |
| T4-PA (2, 3) | Nude NIH Swiss (inbred) | 4 | One died after 29 days, one had metastases near the liver, lungs and in the neck region after 24 days; one had tumor at base of tail, metastases in intestines and near spleen after 30 days; one had met on right hind leg and lower groin area after 31 days. Cells cultured from these lesions failed to thrive. |

[a]n.a. not available.

Example 7

T3-HA Metastatic Cells from Distant Liver Metastasis in Nude NIH Swiss Mouse

T2-A cells ($1 \times 10^6$/mouse) were injected into the tail veins of four immune compromised nude NIH/Swiss mice. Each week one mouse was dissected to determine the existence of metastatic lesions. At 3.5 weeks, a mouse was sacrificed and observed to contain a metastatic lesion in both the liver and a lung. Both tumors were excised, minced, cultured and designated T3-HA (H=hepatic) and T3-PA (P=pulmonary) cells, respectively. Therefore, these cell lines were derived from the local metastatic type T2-A cells migrating from the tail vein injection site of the nude mouse to the liver (T3-HA) or to the lung (T3-PA) to form distant metastatic lesions. This showed that the T2-A cells were capable of metastasizing to distant locations in the nude NIH/Swiss mice. This illustrated the first distant metastatic property by the T2-A cells and the establishment of the T3-HA and T3-PA metastasized cell lines in this tumor progression model. WGC and SKY analysis of T2-A and these two metastatic cell lines generated in vivo in a single mouse might indicate which chromosomal arrangements were common or not between populations of each cell line. These analyses would provide interesting aspects of chromosomal arrangements related to metastatic potential of T2-A cells in vivo giving rise to two cell lines, each derived from the T2-A cell line, that grew simultaneously in separate liver or lung microenvironments in the same mouse.

Example 8

T4-PA Metastatic Cells from Distant Lung Metastasis in Nude NIH Swiss Mouse

To determine if the T3-HA (liver derived) cells from the first distant metastatic liver lesion would go to the liver and generate second metastatic lesions in the liver, $0.7 \times 10^6$ T3-HA cells were injected into the tail veins of four NIH/Swiss nude mice. [T3-PA (lung derived) cells were not tested.] Each week one mouse was dissected to determine metastatic lesions. After 4 weeks, a metastatic lesion occurred in the lung of one mouse. The lesion was excised, minced, cultured and designated T4-PA (P=pulmonary) cell line. This T4-PA cell line was derived from a tumor that had formed from hepatic derived metastatic cells migrating from the tail vein injection site to the lung leaving the circulation to form a metastatic lesion, thereby showing that the T3-HA cells were capable of metastasizing to a distant location other than the liver in the nude NIH/Swiss mice. This illustrated the distant metastatic property of the T3-HA cells and the establishment of the T4-PA metastasized cell lines in this tumor progression model.

Example 9

Overall Comparisons of Tumorigenic and Metastatic Properties

Further studies were undertaken to determine if the T3-HA cells and T4-PA cells metastasize to specific sites. After the T1-A and T-1C cell lines were discovered to rapidly produce primary tumors when injected s.c. in immune-competent NIH Swiss outbred mice (Table 1). They were then injected in the tail veins (i.v.) of these NIH/Swiss mice to search for metastatic lesions. These produced only local metastatic lesions near the tail (Table 2). The T2-A cell line was derived from one of these local metastatic lesions. To enhance the opportunity to produce a metastatic lesion, T2-A cells were injected in the tail vein of a group of partially immune-compromised nude NIH Swiss mice (Table 2). This approach with these T2-A cells, derived from a single local metastasis in a NIH/Swiss mouse, did produce distant metastatic liver, lung, pericardium or throat lesions in nude mice. Cells from a liver lesion were used to establish the T3-HA cell line (and cells from the lung of the same mouse were used to establish the T-3-PA cell line). Thus, this new distant metastatic T3-HA cell line in a nude mouse was derived serially from cells cultured from a local metastatic lesion in a NIH/Swiss mouse. These outcomes (Table 2) indicated that the lung and liver are the most common sites for distant metastasis to occur in nude mice injected i.v. with either the T2-A or T3-HA cells. (As stated above, the T3-PA metastatic cell line has not been evaluated for additional tumorigenic capabilities.) The T4-PA cells were more metastatic than the other cell lines since the few nude mice injected developed lesions in a broader variety of target tissues (Table 2). Although only a few mice were injected with either cell line, the T4-PA cell line appears to more likely have undergone a cellular change allowing it to escape the circulation more easily and invade a broader variety of distant tissues (Table 2). Representative photomicrographs of all the cell types are shown in FIGS. 2A through 2N. Further studies are needed to confirm these initial apparent tumorigenic differences among these new cell lines that have progressed in series from a common origin, the GhrasT-NIH/3T3 cells.

Example 10

Location of the Ras Oncogene in the Cell Lines by PCR

The presence of the human HRAS oncogene was confirmed by PCR amplification using human specific HRAS primers that do not amplify the mouse h-ras proto-oncogene, but do amplify regions of the human proto-oncogene or oncogene (FIG. 3). To determine if any tumors arose from spontaneous tumors and therefore were unrelated to the original GhrasT-NIH/3T3 cell line, four primers for two PCR assays were designed. This spontaneous occurrence was a possibility, since one spontaneous tumor did occur in the nude NIH Swiss mouse colony used to generate nude mice for these studies. Although the coding portion of the c-H-ras-1 gene in mouse, human, rat and hamster are extremely similar, there are significant differences among these species in their gene's three introns [25]. The two PCR primer sets described in the material and methods were able to successfully discriminate between mouse and human h-ras sequences. The human primers only detect either the human c-H-ras-1 oncogene or the human normal proto-oncogene (yielding a 1152 bp PCR product from the 3' nontranslated region). The mouse primers detect only the mouse h-ras proto-oncogene (the *M. musculus* gene for C—H-Ras; yielding a 216 bp PCR product coded in the third intron) present in the NIH/Swiss genome. The normal mouse ras proto-oncogene should only be present in the mouse cells, including the mouse cell lines and mouse liver (control). The human H-ras oncogene should only be in the GhrasT-NIH/Swiss, T1-A, T2-A, T3-HA and T4-PA cell lines as well as in human placenta DNA (control) but not in the NIH/Swiss cells or the NIH/3T3 cell line. This pattern of ras detection was observed in all lines tested (FIG. 3). The PCR results confirm that the tumors used to propagate the T1-A, T2-A, T3-HA and T4-PA cell lines in this tumorigenic model were all derived from the GhrasT-NIH/3T3 cells and not produced simply by random spontaneous tumorigenic events, since the human ras oncogene was still found in the T2-A and T4-PA mouse cell lines. The presence of human ras in the T1-C and T3-PA cell lines remains untested since they are not direct precursors to the T2-A or T4-PA cell lines. They are presumed to contain the human ras oncogene as well since there is no obvious occurrence of spontaneous tumors in these studies.

Example 11

Growth Rates of Each Cell Line

Figure 4:
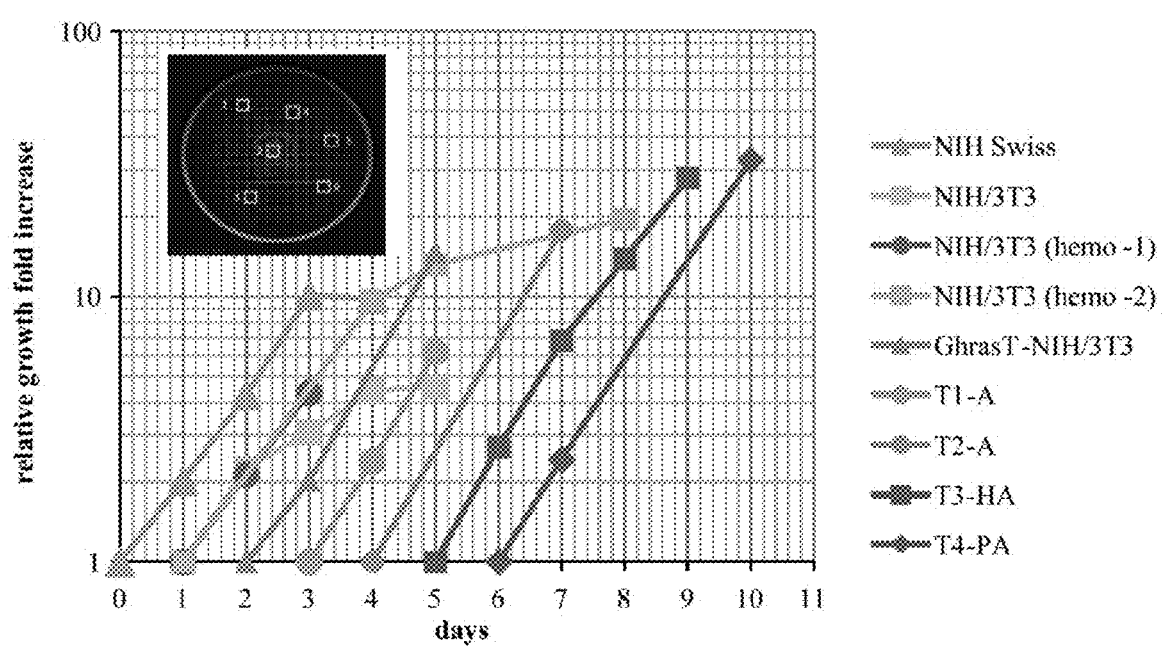
FIG. 4 is a graph plotted using a gridded plate method to determine growth rates for seven cell types. Each cell type was plated, allowed to grow at least one day and fresh media was added. Photomicrographs were recorded at 100× of 6 predetermined 2×2 mm² grids on each plate at the various time intervals indicated. A depiction of selecting random grids for a plate is illustrated in the FIG. 4 insert. The average number of cells in the 6 grids counted in the plate for each cell type each day was determined along with a standard deviation. Relative growth fold increase was determined by normalizing each average cell count to the cell count average of the earliest time point shown in the semi-log graph. To plot all the data on the same graph, the first time point for each cell type was displaced by a one-day on this graph. The graph for each cell type includes some portion of the log phase of growth from which the doubling times were determined as listed in Table 3. The R2 value for each growth curve was determined when possible. Doubling times were determined from each curve and compared, in the case of the NIH/3T3 cells, to the doubling times determined from two experiments using the standard hemocytometer method of counting viable cells harvested each day from 4 multiple plates. Six random grids marked on the bottom of a 60 mm diameter plate with 2×2 mm² grids is depicted here and grids are not shown to scale.

The growth rates (FIG. 4) for each cell line were determined from photomicrographs taken at different times of six pre-specified 2×2 mm² grids on gridded plates in each experiment (FIG. 4 inset). The doubling time in log phase growth for NIH/3T3 cells determined by this new method compared well with values obtained from counting cells by hemocytometry in which cells were harvested from multi-well plates on a daily basis to obtain doubling times (Table 3 and FIG. 4). An advantage of this new method includes the ability to quantify the cell growth within the same six defined areas within a single dish over the period of the experiment. This is accomplished with fewer dishes plated initially and eliminates variations in cell counts inherent in recovering an unequal percentage of cells from replicate dishes in the preparations required to use the hemocytometer. Moreover the cells can be recounted from the photomicrographic records if necessary. The average doubling time of the transformed cells GhrasT-NIH/3T3 (17 h), TIA (17.5 h), T2A (15.5 h), T3-HA (17.5 h) and T4-PA (18.5 h) was 17.2 (st.dev. 1.1 h). The doubling times for the NIH Swiss primary cells and NIH/3T3 cells were 22 h each. Therefore the average doubling time for the transformed cell lines was significantly shorter than that of the non-transformed cell types (P ¼ 0.006). In cell growth inhibitor studies ethanol or DMSO needed to solubilize test compounds can be as high as 0.1% in control cultures without significant growth rate effects compared to growth rates in media without added ethanol or DMSO. (D. B. Ray, pers. comm.).

TABLE 3

Doubling times for normal and transformed cells from photomicrographs or hemocytometer.

| Graph day zero | Cells | Doubling times in hours[a] | Growth curve exponential fit $R^2$ | $R^2$ in log phase data pts used | Counting method |
|---|---|---|---|---|---|
| 0 | NIH Swiss | 22 | 0.99783 | 0, 1, 2, 3 | Gridded plate[b] |
| 1 | NIH/3T3 | 22 | | 1, 2 | Gridded plate |
| 1 | NIH/3T3 | 22 | 0.99966 | 1, 2, 3 | Hemocytometer-1[c] |
| 1 | NIH/3T3 | 22 | | 1, 4 | Hemocytometer-2 |
| | Average for normal | 22 | | | |
| 2 | GhrasT-NIH/3T3 | 17 | 0.99402 | 1, 2, 5 | Gridded plate |
| 3 | T1-A | 17.5 | 0.99939 | 3, 4, 5 | Gridded plate |
| 4 | T2-A | 15.5 | | 4, 7 | Gridded plate |

TABLE 3-continued

Doubling times for normal and transformed cells from photomicrographs or hemocytometer.

| Graph day zero | Cells | Doubling times in hours[a] | Growth curve exponential fit $R^2$ | $R^2$ in log phase data pts used | Counting method |
|---|---|---|---|---|---|
| 5 | T3-HA | 17.5 | 0.99956 | 5, 6, 7 | Gridded plate |
| 6 | T4-PA | 18.5 | 0.99997 | 7, 9, 11 | Gridded plate |
|  | Average for transformed | 17.2 |  |  |  |
|  | Std dev | 1.095 |  |  |  |

P value = 0.0006 between average normal cell and average transformed cell doubling.
[a]Cells were grown and photographed or harvested at defined time intervals to obtain cell counts in log phase.
[b]Data was obtained from photographs of six grids on gridded plates.
[c]Cells were harvested daily from places and live cells, showing trypan blue exclusion, were counted in 4 chambers of a hemocytometer.

REFERENCES

[1] A. Adey, J. N. Burton, J. O. Kitzman, J. B. Hiatt, A. P. Lewis, B. K. Martin, . . . J. Shendure, The haplotype-resolved genome and epigenome of the aneuploid HeLa cancer cell line, Nature 500 (7461) (2013) 207-211, http://dx.doi.org/10.1038/nature12064 ⟨http://www.nature.com/nature/journal/v500/n7461/abs/nature12064.html-supplementary-information⟩.

[2] Sylvan C. Baca, D. Prandi, Michael S. Lawrence, Juan M. Mosquera, A. Romanel, Y. Drier, . . . Levi A. Garraway, Punctuated evolution of prostate cancer genomes, Cell 153 (3) (2013) 666-677.

[3] S. C. Bernstein, R. A. Weinberg, Expression of the metastatic phenotype in cells transfected with human metastatic tumor DNA, Proc. Natl. Acad. Sci. USA 88 (6) (1985) 1726-1730.

[4] F. Z. Bischoff, L. C. Strong, S. O. Yim, D. R. Pratt, M. J. Siciliano, B. C. Giovanella, M. A. Tainsky, Tumorigenic transformation of spontaneously immortalized fibroblasts from patients with a familial cancer syndrome, Oncogene 6 (2) (1991) 183-186.

[5] L. B. Davis, W. M. Kuehl, J. F. Battey, Basic Methods in Molecular Biology, Elsevier Press, New York, 1986.

[6] V. Espina, L. A. Liotta, What is the malignant nature of human ductal carcinoma in situ?Nat. Rev. Cancer 11 (1) (2011) 68-75, http://dx.doi.org/10.1038/nrc2950.

[7] M. Goldfarb, K. Shimizu, M. Perucho, M. Wigler, Isolation and preliminary characterization of a human transforming gene from T24 bladder carcinoma cells, Nature 296 (5856) (1982) 404-409.

[8] R. G. Greig, T. P. Koestler, D. L. Trainer, S. P. Corwin, L. Miles, T. Kline, . . . G. Poste, Tumorigenic and metastatic properties of "normal" and ras-transfected NIH/3T3 cells, Proc. Natl. Acad. Sci. USA 82 (11) (1985) 3698-3701.

[9] H. H. Heng, J. B. Stevens, G. Liu, S. W. Bremer, K. J. Ye, P. V. Reddy, . . . C. J. Ye, Stochastic cancer progression driven by non-clonal chromosome aberrations, J. Cell Physiol. 208 (2) (2006) 461-472, http://dx.doi.org/10.1002/jcp.20685.

[10] J. L. A. Jainchil, S. A. Aaronson, G. J. Todaro, Murine sarcoma and leukemia viruses: assay using clonal lines of contact-inhibited mouse cells, J. Virol. 4 (1969) 549.

[11] V. M. Kavsan, V. P. Baklaushev, O. V. Balynska, A. V. Iershov, P. O. Areshkov, G. M. Yusubalieva, . . . V. P. Chekhonin, Gene encoding chitinase 3-like 1 protein (CHI3L1) is a putative oncogene, Int. J. Biomed. Sci. 7 (3) (2011) 230-237.

[12] H. Korkaya, M. S. Wicha, HER2 and breast cancer stem cells: more than meets the eye, Cancer Res. 73 (12) (2013) 3489-3493, http://dx.doi.org/10.1158/0008-5472.can-13-0260.

[13] K. Koziel, J. Smigelskaite, A. Drasche, M. Enthammer, M. I. Ashraf, S. Khalid, J. Troppmair, RAF and antioxidants prevent cell death induction after growth factor abrogation through regulation of Bcl-2 proteins, Exp. Cell Res. 319 (17) (2013) 2728-2738.

[14] J. J. M. Landry, P. T. Pyl, T. Rausch, T. Zichner, M. M. Tekkedil, A. M. Stütz, . . . L. M. Steinmetz, The genomic and transcriptomic landscape of a HeLa cell line, G3: Genes|Genomes|Genet. 3 (8) (2013) 1213-1224, http://dx.doi.org/10.1534/g3.113.005777.

[15] G. Leprivier, M. Remke, B. Rotblat, A. Dubuc, A. Mateo, F. Rachele, M. Kool, . . . Poul H. Sorensen, The eEF2 kinase confers resistance to nutrient deprivation by blocking translation elongation, Cell 153 (5) (2013) 1064-1079.

[16] L. A. Liotta, H-ras p21 and the metastatic phenotype, J. Natl Cancer Inst. 80 (1988) 468-469.

[17] Littlefield, J. W., 1982. NIH/3T3 Editorial Comment ⟨Science-1982-LITTLEFIELD-214-6.pdf⟩.

[18] G. Liu, J. B. Stevens, S. D. Horne, B. Y. Abdallah, K. J. Ye, S. W. Bremer, . . . H. H. Heng, Genome chaos: survival strategy during crisis, Cell Cycle 13 (4) (2014) 528-537, http://dx.doi.org/10.4161/cc.27378.

[19] S. Liu, Y. Cong, D. Wang, Y. Sun, L. Deng, Y. Liu, . . . M. S. Wicha, Breast cancer stem cells transition between epithelial and mesenchymal states reflective of their normal counterparts, Stem Cell Rep. 2 (1) (2014) 78-91, http://dx.doi.org/10.1016/j.stemcr.2013.11.009.

[20] T. Lowe, J. Sharefkin, S. Q. Yang, C. W. Dieffenbach, A computer program for selection of oligonucleotide primers for polymerase chain reactions, Nucleic Acids Res. 18 (7) (1990) 1757-1761.

[21] M. Malumbres, M. Barbacid, RAS oncogenes: the first 30 years, Nat. Rev. Cancer 3 (2003) 7-13.

[22] Meeker, L. D., Thompson, H. J., 1985. In: Rein, Robert (Ed.), A Multi-Path Theory of Chemical Carcinogenesis in the Rat Mammary Gland. A. R. Liss, Inc., N. Y., pp. 379-388.

[23] N. Miliaras, Clinical genomics transcends sequencing, Genet. Eng. Biotechnol. News 34 (2014) 18-21.

[24] J. Pan, S.-S. Feng, Targeting and imaging cancer cells by folate-decorated, quantum dots (QDs) loaded nanoparticles of biodegradable polymers, Biomaterials 30 (6) (2009) 1176-1183, http://dx.doi.org/10.1016/j.biomaterials.2008.10.039.

[25] B. Przybojewska, G. Plucienniczak, Nucleotide sequence of c-H-ras-1 gene from B6C3F1 mice, Acta Biochim. Pol. 43 (3) (1996) 575-578.

[26] Y. Pylayeva-Gupta, E. Grabocka, D. Bar-Sagi, RAS oncogenes: weaving a tumorigenic web, Nat. Rev. Cancer 11 (11) (2011) 761-774.

[27] D. B. Ray, F. J. Brenner, M. Show, A. Baker, K. Gleason, J. Gressley, . . . P. Barry, Diagnosis of diseases: sample collection, record keeping, processing techniques for molecular analysis of protein, nuclear and mitochondrial DNA and RNA, in: S. K. Majumdar, J. E. Huffman, F. J. Brenner, A. I. Panah (Eds.), Wildlife Diseases: Landscape Epidemiology, Spatial Distribution and Utilization of Remote Sensing Technology, Pennsylvania Academy of Science, Easton, Pa., 2005, pp. 415-427.

[28] E. P. Reddy, Nucleotide sequence analysis of the T24 human bladder carcinoma oncogene, Science 220 (1983) 1061-1063.

[29] E. P. Reddy, R. K. Reynolds, E. Santos, M. Barbacid, A point mutation is responsible for the acquisition of transforming properties by the T24 human bladder carcinoma oncogene, Nature 300 (5888) (1982) 149-152.

[30] H. Rubin, Growth regulation, reverse transformation, and adaptability of 3T3 cells in decreased Mg2 þ concentration, Proc. Natl. Acad. Sci. 78 (1) (1981) 328-332.

[31] C. Scheel, R. A. Weinberg, Cancer stem cells and epithelial-mesenchymal transition: concepts and molecular links, Sem. Cancer Biol. 22 (5-6) (2012) 396-403, http://dx.doi.org/10.1016/j.semcancer.2012.04.001.

[32] T. Shibue, R. A. Weinberg, Metastatic colonization: settlement, adaptation and propagation of tumor cells in a foreign tissue environment, Sem. Cancer Biol. 21 (2) (2011) 99-106, http://dx.doi.org/10.1016/j.semcancer.2010.12.003.

[33] A. Stepanenko, S. Andreieva, K. Korets, D. Mykytenko, N. Huleyuk, Y. Vassetzky, V. Kavsan, Step-wise and punctuated genome evolution drive phenotype changes of tumor cells, Mutat. Res./Fundam. Mol. Mech. Mutagen. 771 (0) (2015) 56-69, http://dx.doi.org/10.1016/j.mrfmmm.2014.12.006.

[34] P. J. Stephens, C. D. Greenman, B. Fu, F. Yang, G. R. Bignell, L. J. Mudie, . . . P. J. Campbell, Massive genomic rearrangement acquired in a single catastrophic event during cancer development, Cell 144 (1) (2011) 27-40, http://dx.doi.org/10.1016/j.cell.2010.11.055.

[35] J. B. Stevens, G. Liu, B. Y. Abdallah, S. D. Horne, K. J. Ye, S. W. Bremer, . . . H. H. Heng, Unstable genomes elevate transcriptome dynamics, Int. J. Cancer 134 (9) (2014) 2074-2087, http://dx.doi.org/10.1002/ijc.28531.

[36] C. J. Tabin, S. M. Bradley, C. I. Bargmann, R. A. Weinberg, A. G. Papageorge, E. M. Scolnick, . . . E. H. Chang, Mechanism of activation of a human oncogene, Nature 300 (5888) (1982) 143-149.

[37] G. J. Todaro, H. Green, Quantitative studies of the growth of mouse embryo cells in culture and their development into established lines, J. Cell Biol. 17 (1963) 299-313.

[38] C. M. Towne, J. F. Dudt, D. B. Ray, Effect of Mansoa alliacea (bignonaceae) leaf extract on embryonic and tumorigenic mouse cell lines, Journal of Medicinal Plants Research 9 (29) (2015) 799-805, http://dx.doi.org/10.5897/jmpr2015.5823.

[39] D. C. Wallace, weiwei Fan, Vincent Procaccio, Mitochondrial energetics and therapeutics, Ann. Rev. Pathol. Mech. Dis., 5, (2010) 297-348.

[40] Y. Wang, H. Dong, M. Xu, B. Xin, W. Niu, D. Xu, L. Liu, 37-kDa laminin receptor precursor promotes lung adenocarcinoma cell invasion and metastasis by epithelial-to-mesenchymal transition, Cancer Gene Ther. 21 (4) (2014) 150-157, http://dx.doi.org/10.1038/cgt.2014.10.

[41] O. Warburg, On respiratory impairmant in cancer cells, Science 124 (1956) 269-270.

[42] R. A. Weinberg, Coming full circle—from endless complexity to simplicity and back again, Cell 157 (1) (2014) 267-271, doi.

We claim:

1. A mouse cell line designated T3-HA, deposited under the ATCC accession number PTA-123513.

2. A mouse comprising a cell of the cell line T3-HA of claim 1, wherein the cell is injected into the mouse and develops into a metastatic liver or lung tumor in the mouse.

3. The mouse of claim 2, wherein the mouse is immunocompromised.

4. The mouse of claim 3, wherein the mouse is a nude NIH Swiss mouse.

5. A mouse cell line designated T4-PA, deposited under the ATCC accession number PTA-123514.

6. A mouse comprising a cell of the cell line T4-PA of claim 5, wherein the cell is injected into the mouse and develops into more than one distant metastatic tumors in more than one organs or extremities in the mouse.

7. The mouse of claim 6, wherein the injected cell develops into more than one distantly metastatic tumors within 21-24days of injection.

8. The mouse of claim 6, wherein the mouse is immunocompromised.

9. The mouse of claim 8, wherein the mouse is a nude NIH Swiss mouse.

10. A method for producing a series of mice with increasingly aggressive tumors, the method compromising:
   a. injecting at least one cell from a cell line having all of the characteristics of the cell line designated T1-A, deposited under ATCC accession number PTA-123697- subcutaneously into a first mouse, wherein the first mouse develops a primary tumor;
   b. injecting at least one cell from the T1-A cell line of (a) intravenously into a second mouse, wherein the second mouse develops a locally metastatic tumor;
   c. injecting at least one cell from a cell line having all of the characteristics of the cell line designated T2A, deposited under ATCC accession number PTA-123698- intravenously into a third mouse, wherein the third mouse develops a distantly metastatic tumor;
   d. injecting at least one cell from a cell line having all of the characteristics of the cell line designated T3-PA, deposited under ATCC accession number PTA-123699 intravenously into a fourth mouse, wherein the fourth mouse develops a metastatic lung tumor;
   e. injecting at least one cell from a cell line having all of the characteristics of the cell line designated T3-HA, deposited under ATCC accession number PTA-123513 into a fifth mouse, wherein the fifth mouse develops a metastatic liver or lung tumor; and
   f. injecting at least one cell from a cell line having all of the characteristics of the cell line designated T4-PA, deposited under ATCC accession number PTA-123514- intravenously into a sixth mouse, wherein the sixth mouse develops more than one distant metastatic tumors in more than one organs or extremities,
   thereby producing a series of mice with increasingly aggressive tumors.

11. A mouse cell line designated T1-A, deposited under the ATCC accession number PTA-123697.

12. A mouse cell line designated T2-A, deposited under the ATCC accession number PTA-123698.

13. A mouse cell line designated T3-PA, deposited under the ATCC accession number PTA-123699.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Homo sapiens

<400> SEQUENCE: 1
ctgtcttcaa catcccaaat gcc        23

<210> SEQ ID NO 2
<211> LENGTH: 25
<212> TYPE: DNA
<213> ORGANISM: Homo sapiens

<400> SEQUENCE: 2
agtgtggtat tccctggaca aaagg        25

<210> SEQ ID NO 3
<211> LENGTH: 20
<212> TYPE: DNA
<213> ORGANISM: Mus musculus

```
<400> SEQUENCE: 3
ggccttagtt cttcttgtcc                                                    20

<210> SEQ ID NO 4
<211> LENGTH: 20
<212> TYPE: DNA
<213> ORGANISM: Mus musculus

<400> SEQUENCE: 4
aaccaacaca aatagggagc                                                    20
```